(12) United States Patent
Kiilerich

(10) Patent No.: US 11,167,092 B2
(45) Date of Patent: Nov. 9, 2021

(54) DRUG DELIVERY DEVICE WITH DOSE RESET MECHANISM

(71) Applicant: Novo Nordisk A/S, Bagsvaerd (DK)

(72) Inventor: Ebbe Kiilerich, Copenhagen NV (DK)

(73) Assignee: Novo Nordisk A/S, Bagsvaerd (DK)

( * ) Notice: Subject to any disclaimer, the term of this patent is extended or adjusted under 35 U.S.C. 154(b) by 337 days.

(21) Appl. No.: 15/551,725

(22) PCT Filed: Feb. 25, 2016

(86) PCT No.: PCT/EP2016/053965
§ 371 (c)(1),
(2) Date: Aug. 17, 2017

(87) PCT Pub. No.: WO2016/135237
PCT Pub. Date: Sep. 1, 2016

(65) Prior Publication Data
US 2018/0064880 A1   Mar. 8, 2018

(30) Foreign Application Priority Data
Feb. 27, 2015   (EP) ..................................... 15156962

(51) Int. Cl.
*A61M 5/315*   (2006.01)
*A61M 5/20*   (2006.01)

(52) U.S. Cl.
CPC .......... *A61M 5/31535* (2013.01); *A61M 5/20* (2013.01); *A61M 5/3155* (2013.01);
(Continued)

(58) Field of Classification Search
CPC ................ A61M 5/31535; A61M 5/20; A61M 5/31553; A61M 5/31558; A61M 5/31575; A61M 5/31583; A61M 5/31593
See application file for complete search history.

(56) References Cited

U.S. PATENT DOCUMENTS

| 5,104,380 A | 4/1992 | Holman et al. |
| 5,921,139 A | 7/1999 | Yamane |

(Continued)

FOREIGN PATENT DOCUMENTS

| CN | 1509193 A | 6/2004 |
| CN | 1597002 A | 3/2005 |

(Continued)

OTHER PUBLICATIONS

Shimano Inc. "Dealer's Manual—Shifting Lever" Apr. 2013, Gear changing mechanism in a bike, pp. 1-27.

*Primary Examiner* — Lauren P Farrar
(74) *Attorney, Agent, or Firm* — Wesley Nicolas

(57) ABSTRACT

Drug delivery device adapted to expel a set dose, comprising an expelling mechanism with a drive spring, a dose setting mechanism with first and second dose setting ratchet parts, a bias spring as well as control means. The control means is adapted to rotate the second ratchet part in a first direction to thereby set a dose when rotating the dose setting member in the first direction, and move the ratchet parts axially out of engagement with each other when the dose setting member is rotated in the opposite direction. When the first and second ratchet parts have been axially disengaged, the drive spring will rotate the second ratchet part in the second direction to thereby reduce the set dose, the bias spring moving the ratchet parts axially into engagement with each other again, this resulting in the set dose being reduced corresponding to one tooth of the ratchet mechanism.

11 Claims, 13 Drawing Sheets

(52) U.S. Cl.
CPC .... *A61M 5/31553* (2013.01); *A61M 5/31558* (2013.01); *A61M 5/31575* (2013.01); *A61M 5/31583* (2013.01); *A61M 5/31593* (2013.01)

(56) References Cited

U.S. PATENT DOCUMENTS

| | | |
|---|---|---|
| 6,899,699 B2 | 5/2005 | Enggaard |
| 6,936,032 B1 | 8/2005 | Bush, Jr. et al. |
| 7,678,085 B2 | 3/2010 | Graf |
| 7,951,113 B2 | 5/2011 | Kohlbrenner et al. |
| 9,283,325 B2 | 3/2016 | Karlsson |
| 9,517,308 B2 | 12/2016 | Moore et al. |
| 9,533,106 B2 | 1/2017 | Hansen et al. |
| 10,092,705 B2 | 10/2018 | Higgins et al. |
| 10,149,946 B2 | 12/2018 | Bernert |
| 10,286,155 B2 | 5/2019 | Bilton et al. |
| 2009/0254035 A1 | 10/2009 | Kohlbrenner et al. |
| 2009/0254045 A1 | 10/2009 | Jost |
| 2011/0077595 A1 | 3/2011 | Eich et al. |
| 2013/0041322 A1 | 2/2013 | Holmqvist |
| 2013/0204193 A1* | 8/2013 | Holmqvist ............ A61M 5/20 604/189 |
| 2014/0088515 A1 | 3/2014 | Karlsson |
| 2014/0350484 A1 | 11/2014 | Kohlbrenner et al. |

FOREIGN PATENT DOCUMENTS

| | | |
|---|---|---|
| CN | 101094699 A | 12/2007 |
| CN | 102716529 A | 10/2012 |
| CN | 103260674 A | 8/2013 |
| CN | 103517729 A | 1/2014 |
| CN | 203408307 U | 1/2014 |
| CN | 103998077 A | 8/2014 |
| CN | 105073167 A | 11/2015 |
| CN | 105682711 A | 6/2016 |
| EP | 1694387 B1 | 11/2012 |
| JP | 2006507035 A | 3/2006 |
| JP | 2016521187 A | 7/2016 |
| WO | 2006045526 A1 | 5/2006 |
| WO | 2008031235 A1 | 3/2008 |
| WO | 2010089418 A2 | 8/2010 |
| WO | 2011025448 A1 | 3/2011 |
| WO | 2012154110 A1 | 11/2012 |
| WO | 2013/178372 A1 | 12/2013 |
| WO | 2014166912 A1 | 10/2014 |
| WO | 2014184080 A1 | 11/2014 |
| WO | 2015032772 A1 | 3/2015 |
| WO | 2016091843 A1 | 6/2016 |

* cited by examiner

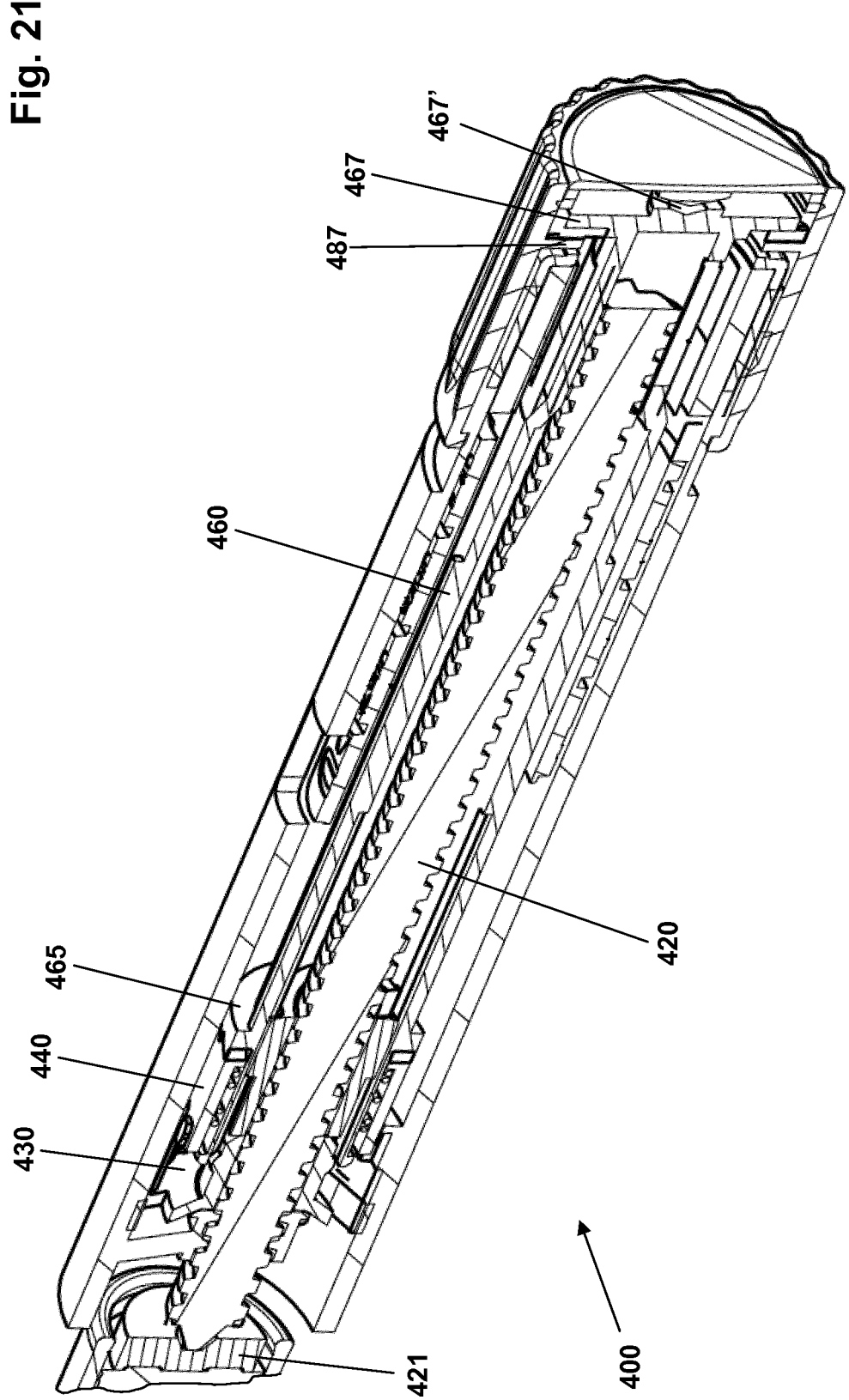

DRUG DELIVERY DEVICE WITH DOSE RESET MECHANISM

CROSS-REFERENCE TO RELATED APPLICATIONS

This application is a 35 U.S.C. § 371 National Stage application of International Application PCT/EP2016/053965 (published as WO 2016/135237), filed Feb. 25, 2016, which claims priority to European Patent Application 15156962.1, filed Feb. 27, 2015; the contents of which are incorporated herein by reference.

The present invention generally relates to drug delivery devices adapted to expel a user settable dose of drug from a cartridge. In a specific aspect the invention relates to a spring-driven device of the wind-up type.

BACKGROUND OF THE INVENTION

In the disclosure of the present invention reference is mostly made to the treatment of diabetes, however, this is only an exemplary use of the present invention.

A general type of drug delivery devices suitable for delivery of a user set amount of drug comprises a spring which is strained during dose setting, the stored energy subsequently being used to expel the set dose of drug from a cartridge arranged in the device. The user usually strains a spring by rotating a rotatable dose setting member, the force thereby applied by the user being stored in the spring for later release.

An example of a known "wind-up" device having a pen-formed configuration and applying a torsion spring is disclosed in U.S. Pat. No. 5,104,380. In this wind-up device, or "auto-pen", the dose setting member is located at the proximal end and works such that when the user rotates the dose setting member the spring is strained and maintained in this strained position until the user releases the set dose by activating the latch provided on the side of the housing. The wind-up pen disclosed in U.S. Pat. No. 5,104,380 has the disadvantage that if a user sets a dose too large it is not possible to decrease the set dose. The user then has to release the latch mechanism thereby expelling the entire set dose before a new correct dose can be set and delivered.

Addressing this problem, wind-up pens in which the user can actually decrease the set dose prior to dosing has been proposed, see e.g. WO 2006/045526 and WO 2010/089418.

These "automatic" delivery devices are based on a spring which is tightened during dose setting and thereafter released to inject the set dose. If a user erroneously sets a dose higher than needed these injection devices has the possibility of lowering the set dose by rotating the dose setting member in an opposite rotational direction. Such dial-down mechanisms can therefore save the user from expelling expensive drug due to an erroneous dose setting.

In WO 2006/045526, the dial-up/dial-down mechanism is based on a flexible ratchet arm which is locked in a one-way engagement with a toothed ring. When the user sets a dose the dose setting button provided at the proximal end of the delivery device is rotated. This dose setting button is connected to the ratchet element via a longitudinal stretching tubular sleeve. The ratchet element is provided with a ratchet arm in a toothed engagement with the toothed ring such that the ratchet arm when the dose setting button is rotated locks against the force of the torsion spring in the subsequent teeth of the toothed ring thereby straining the torsion spring in incremental steps. In order to reduce the set size, the ratchet arm is actively pulled out of engagement with the toothed ring whereby the force accumulated in the torsion spring rotates the ratchet element rapidly backwards such that the ratchet arm engages the previous tooth in the toothed ring thereby lowering the set dose with one increment. The FlexTouch® and FlexPro® drug delivery devices provided by Novo Nordisk, Bagsværd, Denmark comprise a ratchet mechanism of the type disclosed in WO 2006/045526. WO 2011/025448 discloses a further drug delivery device comprising a ratchet mechanism of this type.

The dial-down arrangement known from WO 2006/045526 could be referred to as being an "active" dial-down arrangement as the ratchet arm needs to be radially and actively moved free of its toothed engagement in order to dial down the set dose size. US 2013/0204193 discloses a spring-driven drug delivery device comprising a ratchet mechanism which can be reset by manually pulling the ratchet members apart. An example of a "passive" dial-down arrangement is known from e.g. WO 2008/031235 disclosing a dose setting mechanism with a two-way ratchet.

Having regard to the above, it is an object of the present invention to provide a drug delivery device having a resettable dose setting mechanism which is accurate, simple and reliable. It is a further object to provide a resettable dose setting mechanism which is compact in design and allows a high degree of freedom of design for the drug delivery device in which it is incorporated just as it should allow for cost-effective manufacturing.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a general aspect of the invention a drug delivery device is provided comprising a housing and an expelling assembly with dose setting means. The expelling assembly comprises a piston rod adapted to engage and axially displace a piston in a loaded cartridge in a distal direction to thereby expel a dose of drug from the cartridge, a drive member defining a reference axis, a drive spring coupled to the drive member, dose setting means allowing a user to simultaneously set a dose amount to be expelled and strain the drive spring correspondingly by rotation of the drive member, and release means adapted to release the strained drive spring to rotate the drive member to expel the set dose amount. The dose setting means comprises a dose setting member adapted to rotate in a first direction to set a dose, and rotate in an opposed second direction to reduce a set dose, and a releasable one-way ratchet mechanism allowing the drive member to be rotated in the first direction. The one-way ratchet mechanism comprises a first ratchet part comprising a plurality of ratchet teeth, the first ratchet part being non-rotationally coupled to the housing during dose setting, a second ratchet part comprising a plurality of ratchet teeth adapted to rotationally engage the ratchet teeth on the first ratchet part, the second ratchet part being non-rotationally coupled to the drive member during dose setting, the first and second ratchet parts being axially moveable relative to each other during dose setting, bias means for axially biasing the first and second ratchet parts into engagement with each other, control means adapted to rotate the second ratchet part in the first direction to thereby set a dose when the dose setting member is rotated in the first direction, and move the first and second ratchet parts axially out of engagement with each other when the dose setting member is rotated in the second direction. When the first and second ratchet parts have been axially dis-engaged, the drive spring will rotate the second ratchet part in the second direction to thereby reduce the set dose, the bias means moving the first and second ratchet parts axially into engagement with each other again, this resulting in the set dose being reduced corresponding to one tooth of the ratchet mechanism.

By the above arrangement a ratchet mechanism for a spring-driven drug delivery device is provided which is simple and reliable and which can be implemented in numerous ways. The drive spring may be in the form of e.g. a helical torsion spring, a clock-type torsion spring or a helical compression spring. Also the bias means may be in the form of a helical spring.

In exemplary embodiments the control means comprises a drive-release ratchet having a plurality of ratchet drive surfaces and a plurality of ratchet release surfaces inclined relative to a rotational reference plane (i.e. a plane perpendicular to the reference axis), as well as a control ratchet comprising a plurality of control drive surfaces and a plurality of control release surfaces inclined relative to the rotational reference plane. In such an arrangement the control drive surfaces are cooperating with the ratchet drive surfaces to rotate the second ratchet part in the first direction when the dose setting member is rotated in the first direction, and the control release surfaces are slidingly cooperating with the ratchet release surfaces to axially move the first and second ratchet parts axially out of engagement with each other when the dose setting member is rotated in the second direction.

By the above arrangement a drive-release mechanism for the above-described ratchet mechanism is provided which is simple and reliable and which can be implemented in numerous ways.

In a further general aspect of the invention a drug delivery device is provided comprising, or being adapted to receive, a drug-filled cartridge, a housing and an expelling assembly. The expelling assembly comprises a piston rod adapted to engage and axially displace a piston in a loaded cartridge in a distal direction to thereby expel a dose of drug from the cartridge, a drive member defining a reference axis, a drive spring coupled to the drive member, dose setting means allowing a user to simultaneously set a dose amount to be expelled and strain the drive spring correspondingly by rotation of the drive member, and release means adapted to release the strained drive spring to rotate the drive member to expel the set dose amount. The dose setting means comprises a dose setting member adapted to rotate in a first direction to set a dose, and rotate in an opposed second direction to reduce a set dose, and a releasable one-way ratchet mechanism allowing the drive member to be rotated in the first direction. The ratchet mechanism comprises a first ratchet part comprising a plurality of ratchet teeth, the first ratchet part being non-rotationally coupled to the housing during dose setting, a second ratchet part comprising a plurality of ratchet teeth adapted to rotationally engage the ratchet teeth on the first ratchet part, the second ratchet part being non-rotationally coupled to the drive member during dose setting, the first and second ratchet parts being axially moveable relative to each other during dose setting, and bias means for axially biasing the first and second ratchet parts into engagement with each other. The dose setting means further comprises control means adapted to rotate the second ratchet part in the first direction to thereby set a dose when the dose setting member is rotated in the first direction, and move the first and second ratchet parts axially out of engagement with each other when the dose setting member is rotated in the second direction. The control means comprises a drive-release ratchet having a plurality of ratchet drive surfaces and a plurality of ratchet release surfaces inclined relative to a rotational reference plane, and a control ratchet comprising a plurality of control drive surfaces and a plurality of control release surfaces inclined relative to the rotational reference plane. The control drive surfaces are cooperating with the ratchet drive surfaces to rotate the second ratchet part in the first direction when the dose setting member is rotated in the first direction, and the control release surfaces are slidingly cooperating with the ratchet release surfaces to axially move the first and second ratchet parts axially out of engagement with each other when the dose setting member is rotated in the second direction. Thereby, when the first and second ratchet parts have been axially dis-engaged, the drive spring will rotate the second ratchet part in the second direction to thereby reduce the set dose, the bias means moving the first and second ratchet parts axially into engagement with each other again, this resulting in the set dose being reduced corresponding to one tooth of the ratchet mechanism.

In a first specific aspect of the invention the first ratchet part is integral with the housing, and the second ratchet part is rotationally released from the drive member during dose expelling. When the drug delivery device further is provided with the above-described drive-release mechanism, the drive-release ratchet may be integral with the second ratchet part, and the control ratchet may be integral with the dose setting member. The ratchet drive surfaces, the ratchet release surfaces and the second ratchet part teeth may be arranged on the same circumference. When it is defined that two structures are integral they may e.g. be formed integrally or rigidly connected.

In a second specific aspect of the invention when a drug delivery device is provided with the above-described drive-release mechanism the first ratchet part is integral with the housing, the second ratchet part is rotationally released from the drive member during dose expelling, the drive-release ratchet is integral with the second ratchet part, and the control ratchet is coupled non-rotationally but axially moveable to the dose setting member.

In an exemplary embodiment the dose setting member is a combined dose setting and release member being moveable from a proximal dose setting position to a distal spring release position.

In a third specific aspect of the invention the first ratchet part is axially moveable relative to the housing, and the second ratchet part is integral with the drive member. The first ratchet part may be moveable from a proximal dose setting position in which it is non-rotationally coupled to the housing, to a distal spring release position in which it is allowed to rotate relative to the housing.

When the drug delivery device further is provided with the above-described drive-release mechanism, the drive-release ratchet may be integral with the drive member, and the control ratchet may be integral with the dose setting member.

In an exemplary embodiment the dose setting member is a combined dose setting and release member being moveable from a proximal dose setting position to a distal spring release position.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following the invention will be further described with reference to the drawings, wherein FIG. 21 shows in cross-section the third exemplary embodiment in an assembled state.

In the figures like structures are mainly identified by like reference numerals.

DESCRIPTION OF EXEMPLARY EMBODIMENTS

Figure 1A:
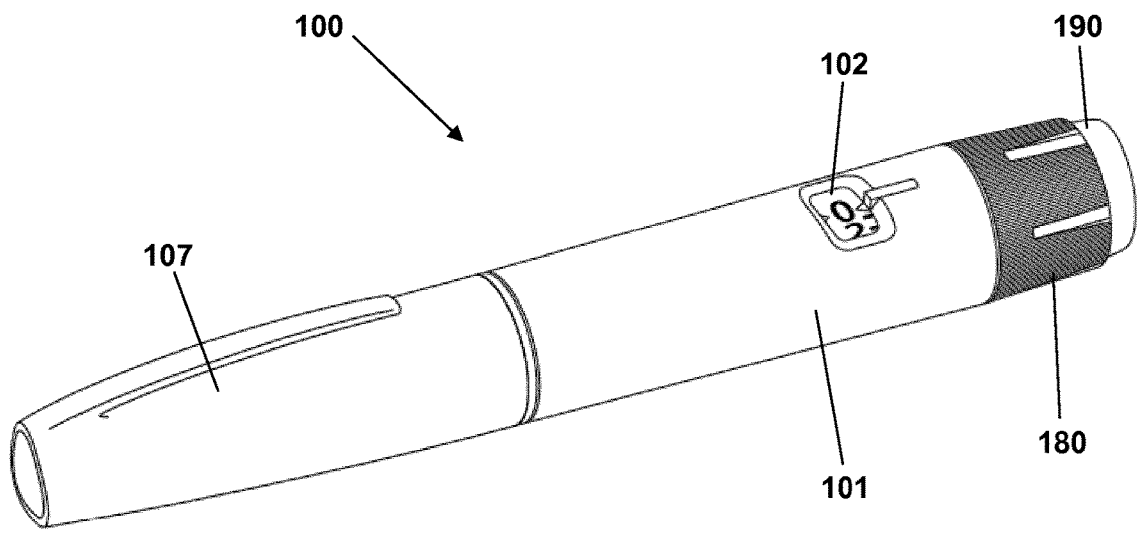
FIGS. 1A and 1B show an embodiment of a drug delivery device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to embodiments of the present invention per se, an example of a "generic" resettable dial-up/dial down automatic drug delivery device will be described, such a device providing the basis for the exemplary embodiment of the present invention.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a cartridge holder attached to the proximal portion, the cartridge holder having openings allowing a portion of the cartridge to be inspected. Distal coupling means 115 allows a needle assembly to be releasably mounted in fluid communication with the cartridge interior. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. Depending on the type of expelling mechanism embodied in the drug delivery device, the expelling mechanism may comprise a torsion spring as in the shown embodiment which is strained during dose setting and then released to drive the piston rod when the release button is actuated. Alternatively a compression spring may be used, e.g. as disclosed in EP2015/080904. More specifically, during dose setting a drive member to which the spring is connected is rotated to a rotational position corresponding to the set dose, the drive member thereby being in an energized state. A scale drum with dose size numerals is coupled to the drive member such that the size of the currently set dose is shown in the display window, e.g. by means of a threaded connection with the housing. To prevent the drive member from rotating the dose setting mechanism is provided with a holding mechanism, which in the shown embodiment is in the form of a ratchet mechanism. When the user desires to expel the set dose the button is actuated whereby the drive member is brought into engagement with the piston rod drive mechanism and the holding mechanism subsequently released.

Figure 1B:
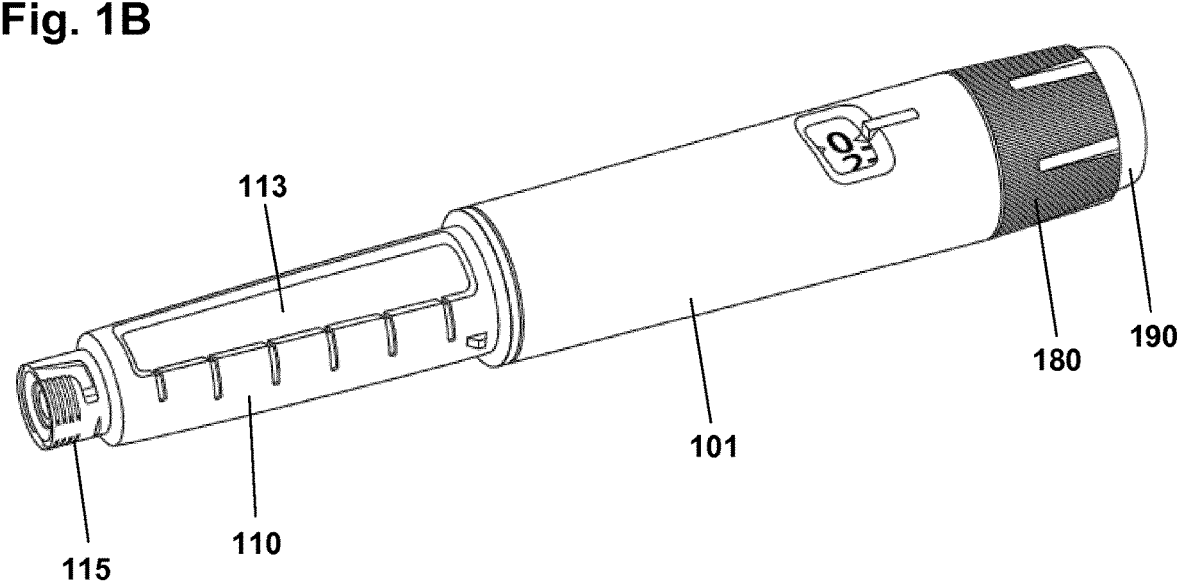

Although FIGS. 1A and 1B show a drug delivery device of the pre-filled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

With reference to FIGS. 2-6 a first exemplary embodiment of the present invention per se, a resettable dose setting mechanism for a drug delivery device, will be described.

The mechanism basically comprises a housing portion 201, a drive tube 260, a torsion spring 255 arranged between the housing and the drive tube, a transmission member 240, a dose setting member 280, a release button 290 and a return spring 295.

A detailed description of the working principle of the mechanism will be given below, however, first some of the central components of the dose setting mechanism will be described in detail.

Figure 2:
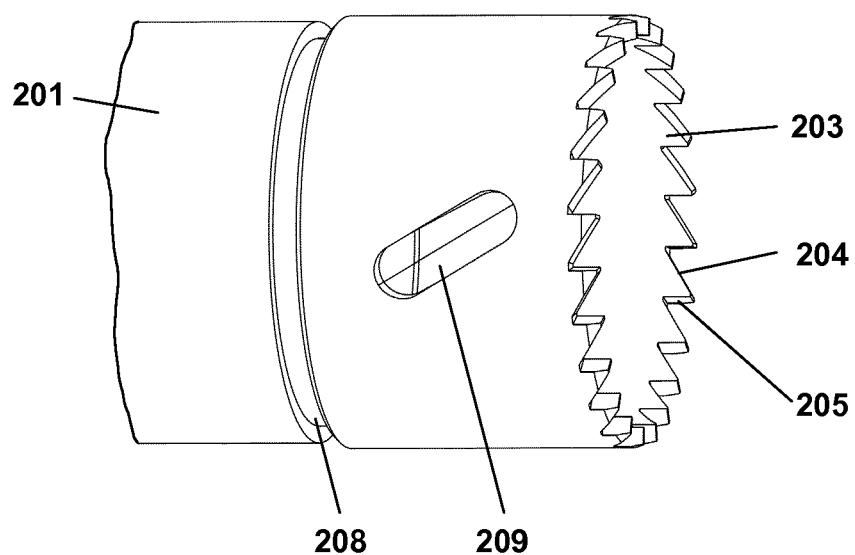
FIG. 2 shows a ratchet part of a first exemplary embodiment of a drug delivery device.

Turning to FIG. 2 a proximal portion of a tubular housing member 201 defining a longitudinal reference axis is shown. The housing member comprises a circumferential proximal edge with a plurality of ratchet teeth structures 203 (here: 24), each tooth having a triangular configuration with an inclined ratchet surface 204 and a stop surface 205 oriented perpendicularly to the housing member cross-sectional plane. The housing further comprises a circumferential groove 208 adapted to engage the dose setting member and arranged between the groove and the proximal end a number of inclined slots 209 (here: three) adapted to engage a spring housing (see below). In this way a first ratchet part coupled non-rotationally to the housing and comprising a plurality of ratchet teeth is formed. As appears, in this embodiment the first ratchet part is formed integrally with the tubular housing member.

Figure 4:
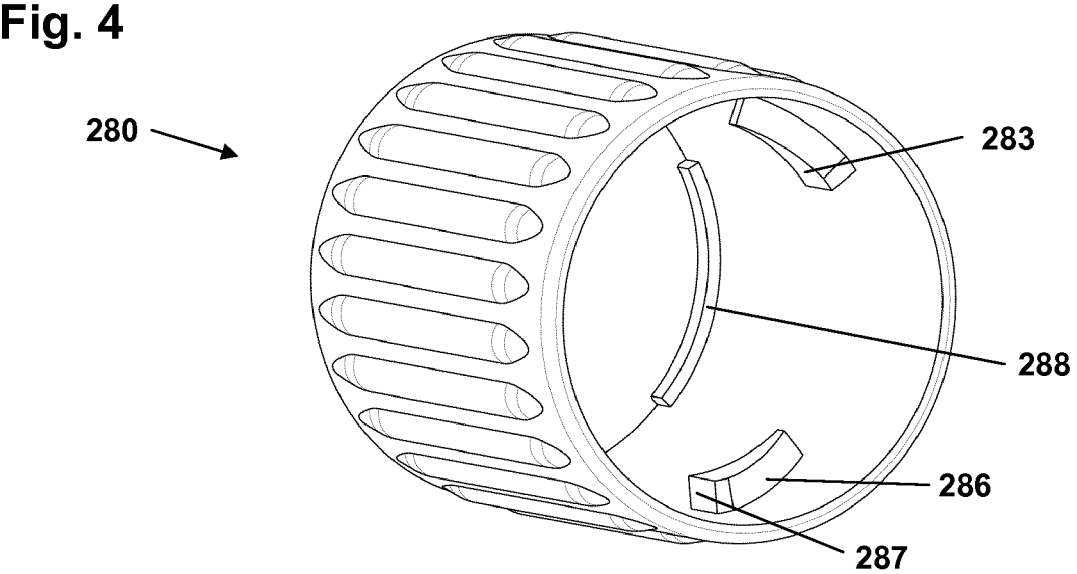
FIG. 4 shows a dose setting member of the first exemplary embodiment.

FIG. 4 shows the dose setting member 280 having a generally tubular configuration with an outer cylindrical surface with a plurality of longitudinally arranged ridges 281 providing a gripping surface, and an inner cylindrical surface comprising a at the distal end a number of circumferential flange portions 288 adapted to be rotationally arranged in the housing member circumferential groove. The inner surface further comprises a number of triangular "drive-release" or "drive-lift" control ratchet structures 283 (here: three) forming a "drive-release" or "drive-lift" control ratchet adapted to engage the transmission member as will be described below, each drive-release or drive-lift control structure comprising a longitudinally oriented drive surface 287 and an inclined lift surface 286. In the following specific description the term "drive-lift" will be used.

Figure 3:
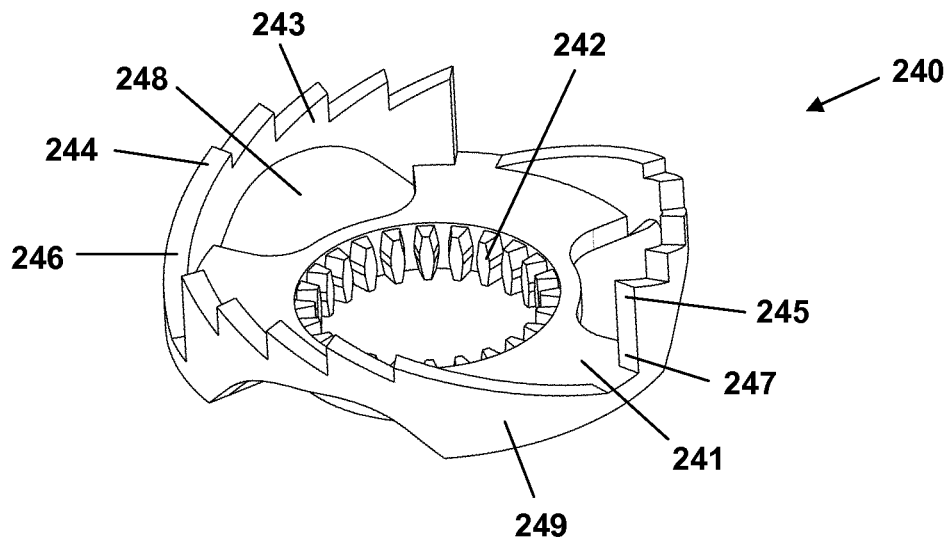
FIG. 3 shows a further ratchet part of the first exemplary.

FIG. 3 shows the transmission member 240 having a ring-shaped body portion 241 with a central opening provided with a plurality of longitudinally arranged splines 242 adapted to slidingly engage corresponding spline grooves on the drive tube. The transmission member further comprises a number of ratchet sections 249 (here: three) between which are formed three drive sections. Each ratchet section comprises a number of ratchet teeth 243 adapted to engage the housing member ratchet teeth 203 to provide a one-way ratchet. In this way a second ratchet part is formed. For a given ratchet section the leading inclined ratchet surface 244 is extended to form a lift surface 246, just as the trailing stop surface 245 is also extended longitudinally to form a drive surface 247. In this way each drive section is defined between an extended ratchet surface and an extended stop surface. Corresponding to each ratchet section an opening 248 is formed in the body portion to allow passage of a release button leg portion (see below).

Figure 5:
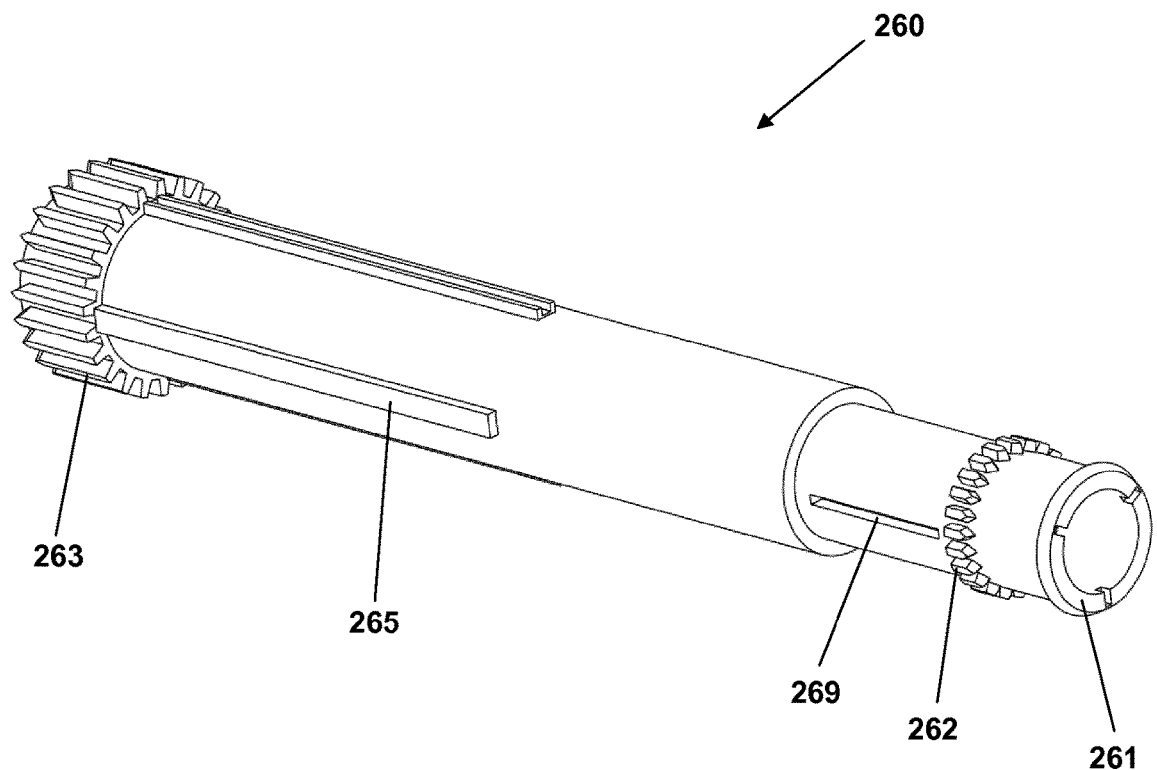
FIG. 5 shows a drive member of the first exemplary embodiment.

FIG. 5 shows the drive tube 260 having a proximal-most circumferential flange 261, a proximal array of circumferential splines 262 and a distal array of circumferential splines 263. The flange is adapted to engage release button snap members 291, the proximal splines are adapted to engage the transmission member splines 242, and the distal splines are coupling splines adapted to axially engage the piston driver 230 during actuation. The drive tube further comprises a slot 269 for attaching the inner end of the drive spring as well as a number of splines 265 adapted to interface with a scale drum. As appears, one of the splines is different allowing it to rotationally mate with a corresponding scale drum spline.

Figure 6:
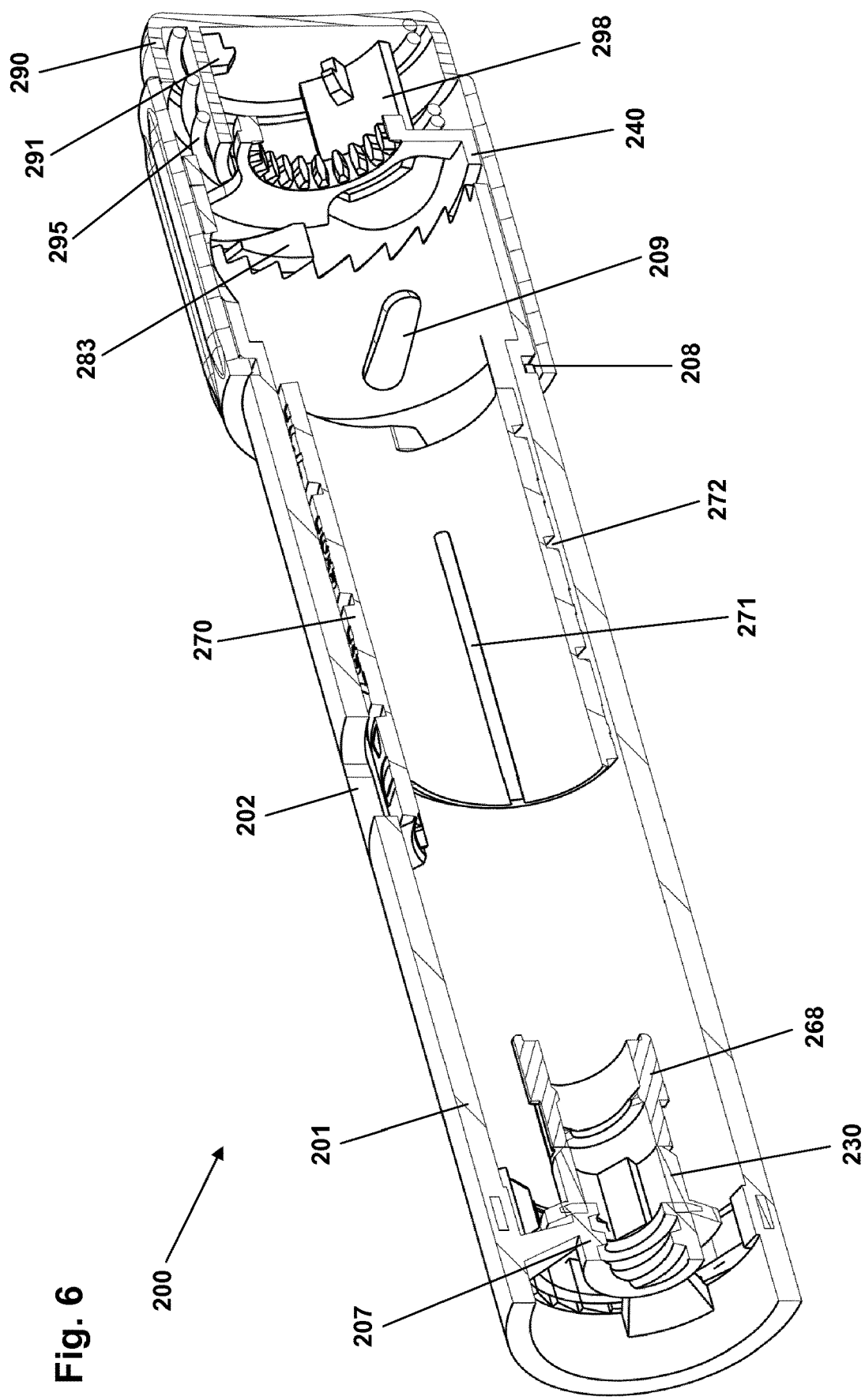
FIG. 6 shows in cross-section the first exemplary embodiment in a partly assembled state.

Turning to FIG. 6 the housing member proximal portion, the dose setting member, the transmission member and the release button are shown in an assembled state. The figure further shows the proximal portion of a scale 270 drum provided with an inner longitudinal spline 271 for engagement with the drive tube and an outer helical groove 272 for threaded connection with the housing inner surface. To allow the ratchet interface to be visible, the drive tube and the torsion spring have been omitted in FIG. 6.

More specifically, the dose setting member 280 is mounted rotationally free but axially locked on the housing member by means of the flanges arranged in the circumferential housing groove 208. The transmission member 240 is mounted non-rotationally on the drive tube (see FIG. 7) by means of a splined connection allowing the transmission member to move axially relative to both the drive tube and the dose setting member. Further, the release button 280 is mounted rotationally free but axially locked to the proximal end of the drive tube by means of a number of snap members 291 engaging the proximal flange 261. The release button further comprises a number of leg portions 298 adapted to be moved through the transmission member openings 248. A bias means in form of a return spring 295 is arranged between the transmission member and the release button, the return spring urging the transmission member ratchet teeth 243 into engagement with the housing member ratchet teeth 203 as shown. As can also be seen in FIG. 6 one of the drive-lift ratchet control structures 283 is arranged corresponding to a transmission member drive section, the two drive surfaces and the two lift surfaces engaging each other. As appears, in the engaged position the ratchet prevents the transmission member, and thus the drive tube, from being turned counter-clockwise.

When setting a dose the dose setting member is rotated clockwise. As the drive surfaces 287 of the drive-lift ratchet control structures 283 are in engagement with the corresponding drive surfaces 247 on the transmission member the latter is forced to rotate together with the dose setting member to the desired rotational position, this resulting in the transmission member ratchet teeth passing over the housing ratchet teeth during which the transmission member is moved back and forth due to the inclined ratchet teeth, the return spring and the splined connection with the drive tube. The dose can be set in increments corresponding to one ratchet tooth which e.g. for a given insulin delivery device typically will correspond to one unit (IU) of insulin formulation.

When decreasing a set dose the dose setting member is rotated counter-clockwise whereby a gap is created between the drive surfaces on the drive-lift ratchet control structure 283 respectively the transmission member. However, as the inclined lift surfaces 286 of the drive-lift control structures are in engagement with the corresponding lift surfaces 246 on the transmission member the latter is moved proximally against the return spring until the transmission member ratchet teeth just disengages the housing ratchet teeth, at which point the force from the strained spring will rotate the drive tube counter-clockwise and thereby also the transmission member, this resulting in the inclined lift surfaces disengaging each other. As a consequence the transmission member can be moved distally by the return spring whereby the ratchet teeth will re-engage, this corresponding to the previously set dose having been decreased by one increment. If the user continuous to rotate the dose setting member counter-clockwise the set dose will continue to be reduced by one increment for each back and forth movement of the transmission member. At the same time the scale drum is also rotated counter-clockwise and the dose size shown in the display window 202 is reduced correspondingly.

Figure 7:
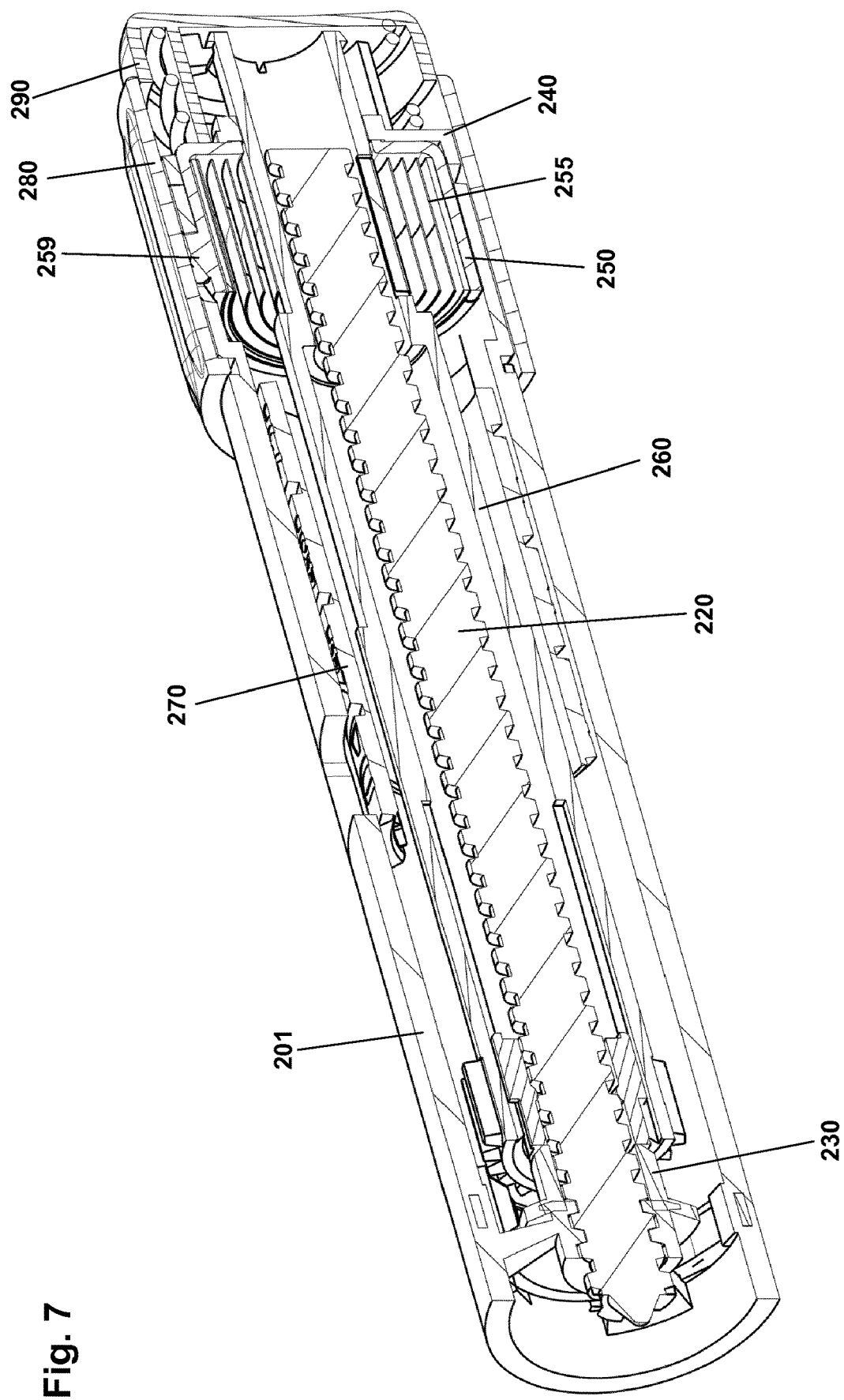
FIG. 7 shows in cross-section the first exemplary embodiment in an assembled state.

Turning to FIG. 7 the figure shows the device of FIG. 6 with further components of the dose setting and expelling mechanism arranged inside the housing 201. More specifically, the figure shows a drive tube 260 in splined connection with the scale drum 270, a clock-type torsion drive spring 255 mounted in a cup-shaped spring housing 250 and connected to the spring housing respectively the drive tube, a threaded piston rod 220 arranged inside the drive tube and being threadedly connected to a stationary housing nut portion 207, a piston driver 230 arranged non-rotatable but axially moveable on the piston rod, as well as a drive coupling 263 allowing the drive tube to be coupled in and out of engagement with the piston driver. The spring housing comprises a number of lateral projections 259 adapted to be slidingly received in the inclined housing slots 209, this allowing the spring housing and spring to be moved axially back and forth as the drive tube is moved back and forth during actuation, the inclined slots together with the spring torque ensuring that the spring housing will be moved proximally when the device is not actuated. The device further comprises an end-of-content member 225 coupled to the piston rod and drive tube.

To expel a set dose of drug the actuation button 290 is moved distally against the force of the return spring whereby firstly the distal end of the drive tube 260 engages the piston driver 230 via the drive coupling and secondly the drive tube splines disengages the transmission member splines 242, this allowing the strained spring 255 to rotate the drive tube and thereto coupled piston driver and piston rod 220 counter-clockwise, this resulting in the piston rod being moved distally through the threaded housing nut 207. When the user releases the pressure on the actuation button the return spring serves to return the button and drive tube in the proximal direction and thereby firstly re-engage the splined connection between the drive tube and the transmission member and secondly dis-engage the drive tube from the piston driver, this movement also allowing a partly expelled dose to be paused.

With reference to FIGS. 8-13 a second exemplary embodiment of the present invention will be described. The mechanism basically comprises a housing member 301, a drive tube 360, a helical torsion spring 355 arranged between the housing and the drive tube, a transmission member 340, a drive-lift control member 390, a combined dose setting and release member 380 and a return spring 395. The main difference between the first and second embodiment is that the functionality of the dose setting member has been split into two members, this allowing the dose setting member to move axially relative to the housing. Otherwise the general working principles of the two embodiments are the same as will be apparent from the detailed description of the working principle given below, however, first some of the central components of the dose setting mechanism will be described in detail.

Figure 8:
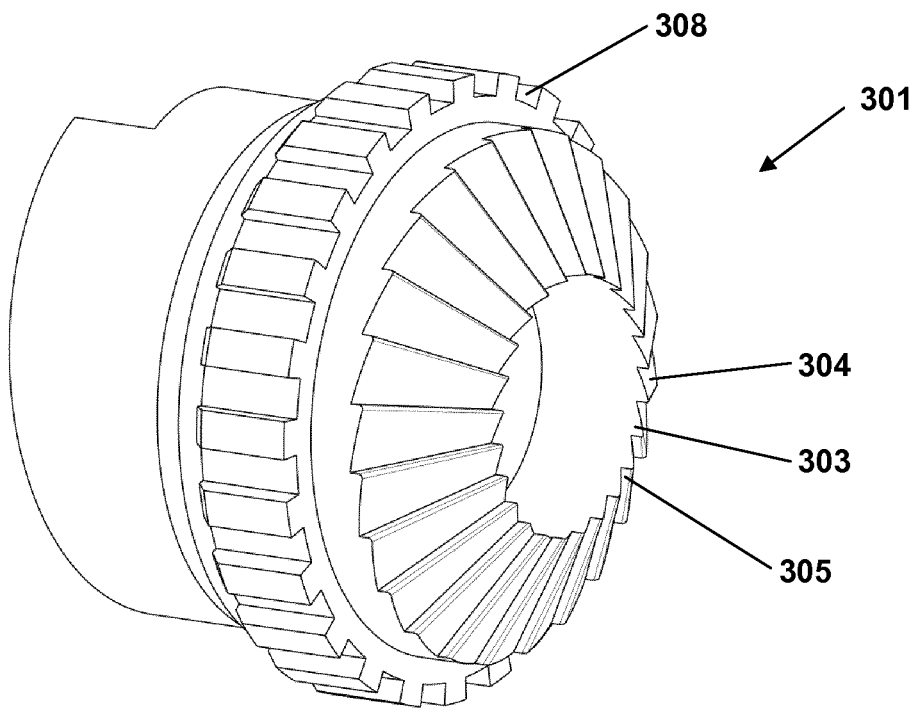
FIG. 8 shows a ratchet part of a second exemplary embodiment of a drug delivery device.

Turning to FIG. 8 a housing base member 301 defining a longitudinal reference axis is shown. The housing base member is attached to the proximal end of a tubular main housing member 309 (see FIG. 12) and forms the base for a drive spring. The housing member comprises a proximally-facing conical surface on which a plurality of ratchet teeth structures 303 (here: 24) is arranged around a central opening, each tooth having a triangular configuration with an inclined ratchet surface 304 and a stop surface 305 oriented perpendicularly to the housing member cross-sectional plane. The housing base member further comprises an outer circumferential array of longitudinal splines 308 adapted to engage the dose setting member. In this way a first ratchet part coupled non-rotationally to the housing and comprising a plurality of ratchet teeth is formed. As appears, in this embodiment the first ratchet part is formed integrally with the housing base member.

Figure 9:
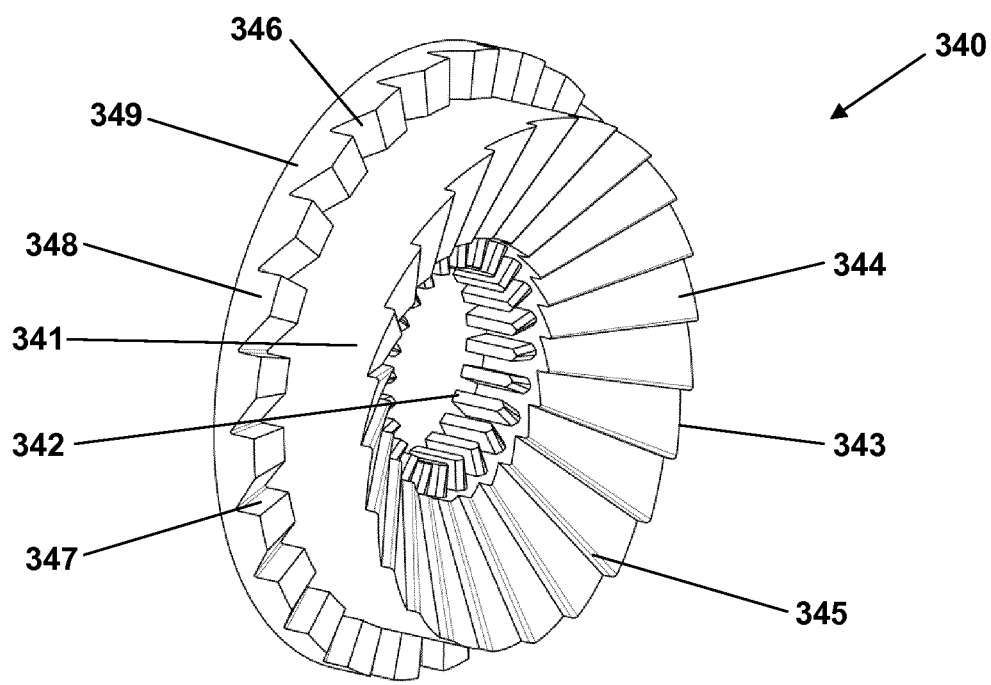
FIG. 9 shows a further ratchet part of the second exemplary.

FIG. 9 shows the transmission member 340 having a ring-shaped body portion 341 with a central opening provided with a plurality of longitudinally arranged splines 342 adapted to slidingly engage corresponding spline grooves on the drive tube. The transmission member comprises a distally-facing (when mounted) concave surface on which a first plurality of ratchet teeth structures 343 (here: 24) is arranged around the central opening, each tooth having a triangular configuration with an inclined ratchet surface 344 and a stop surface 345 oriented perpendicularly to the housing member cross-sectional plane, the ratchet teeth being configured to interface with the corresponding ratchet teeth on the housing member to thereby provide a one-way ratchet. In this way a second ratchet part is formed. The transmission member further comprises an outer circumferential flange 349 with a second plurality (here: 24) of distally-facing (when mounted) ratchet teeth structures 348, each tooth having a configuration with an inclined lift surface 346 and a drive surface 347 oriented perpendicularly to the housing member cross-sectional plane. In the shown embodiment each tooth has a flat top. As appears, compared to the first embodiment the drive-lift surfaces have been separated from the main ratchet structure.

Figure 10:
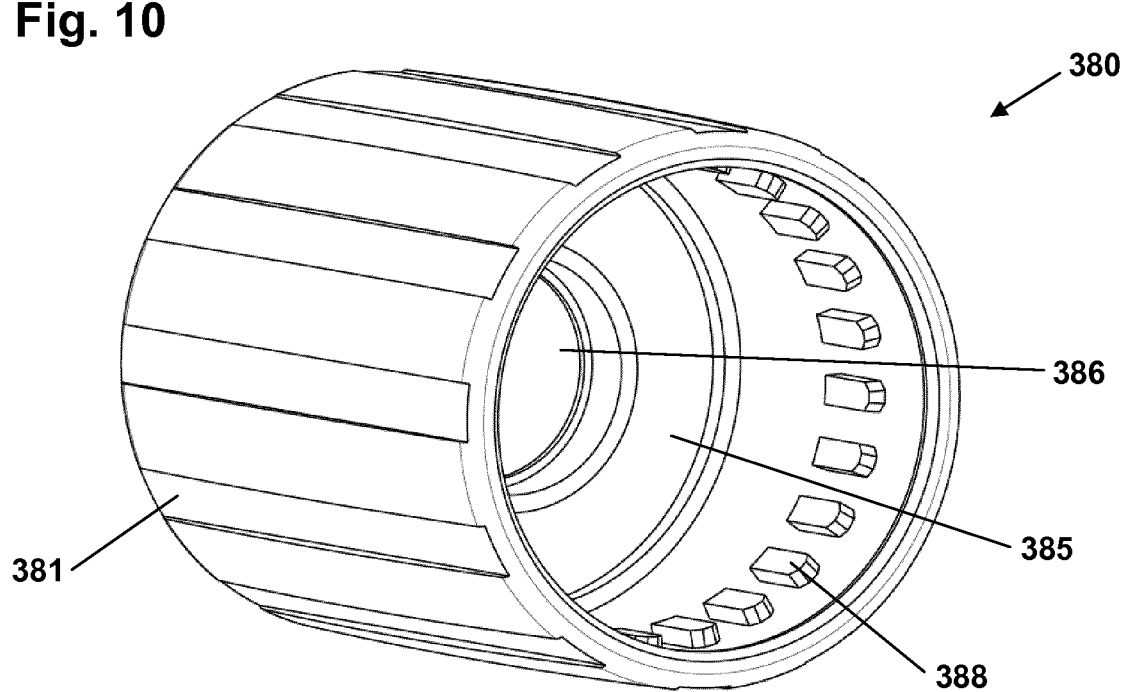
FIG. 10 shows a dose setting member of the second exemplary embodiment.

FIG. 10 shows the dose setting member 380 having a generally tubular configuration with an outer cylindrical surface with a plurality of longitudinally arranged ridges 381 providing a gripping surface, and an inner cylindrical surface comprising at the distal end a number of longitudinally arranged splines 388 adapted to interface with the housing member splines 308. The dose setting member further comprises an inner ring-formed transversal partition wall 385 with a central opening 386 adapted to rotationally interface with the drive tube proximal end.

Figure 11:
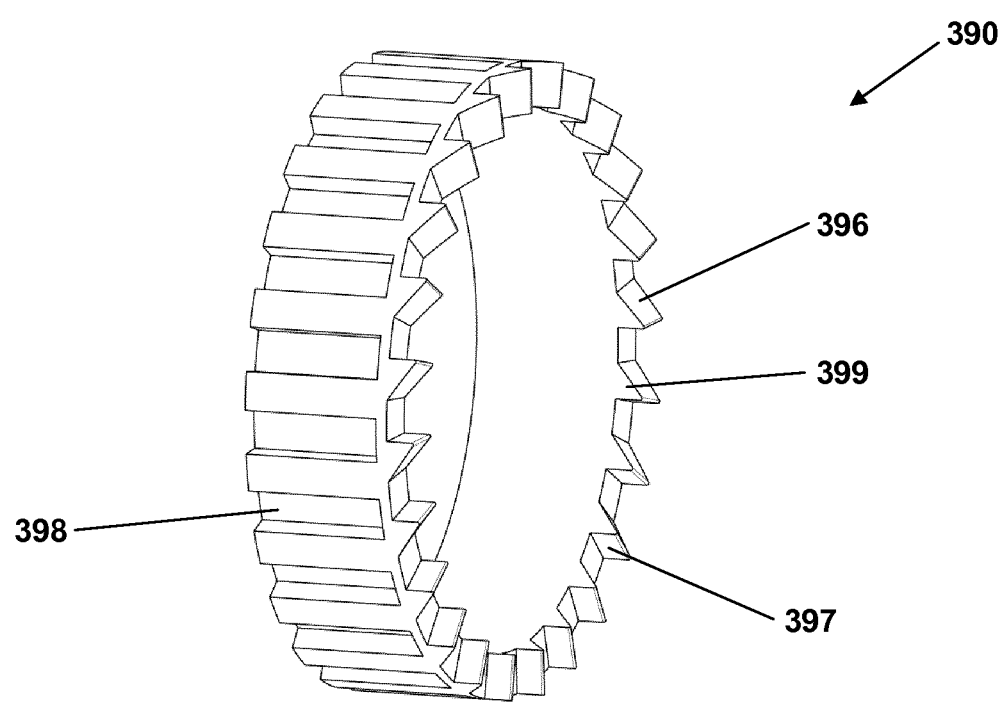
FIG. 11 shows a yet further ratchet part of the second exemplary.

The integrated drive-lift control structures of the first embodiment dose setting member have been transferred to a separate drive-lift control member. More specifically as shown in FIG. 11, the drive-lift member 390 is configured as a ring-formed member having an outer circumferential surface with a plurality of longitudinally arranged splines 398 adapted to interface with the dose setting member splines 388, as well as a plurality of proximally-facing drive-lift teeth 399 arranged on the proximal circumferential edge, each tooth having a triangular form with a longitudinally oriented drive surface 397 and an inclined lift surface 296 adapted to engage the corresponding drive-lift surfaces 347, 346 on the transmission member 340.

Figure 12:
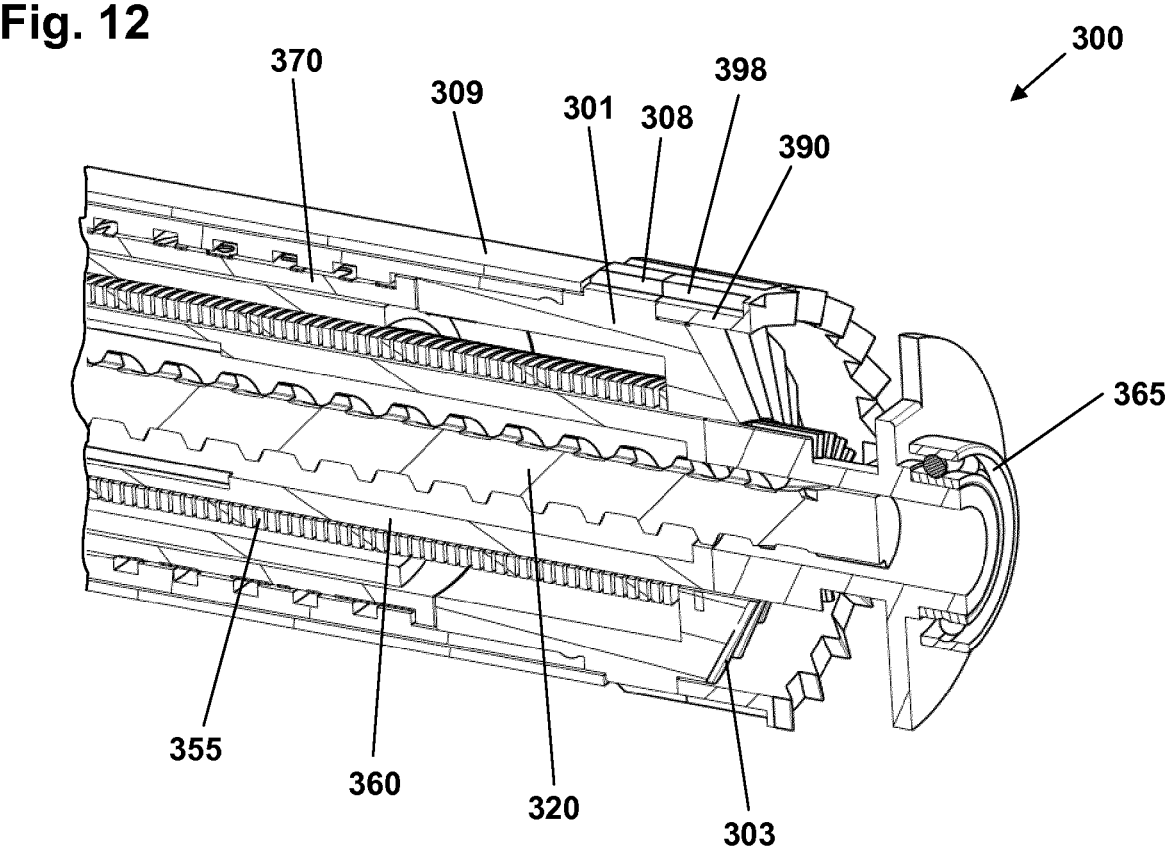
FIG. 12 shows in cross-section the second exemplary embodiment in a partly assembled state.
Figure 13:
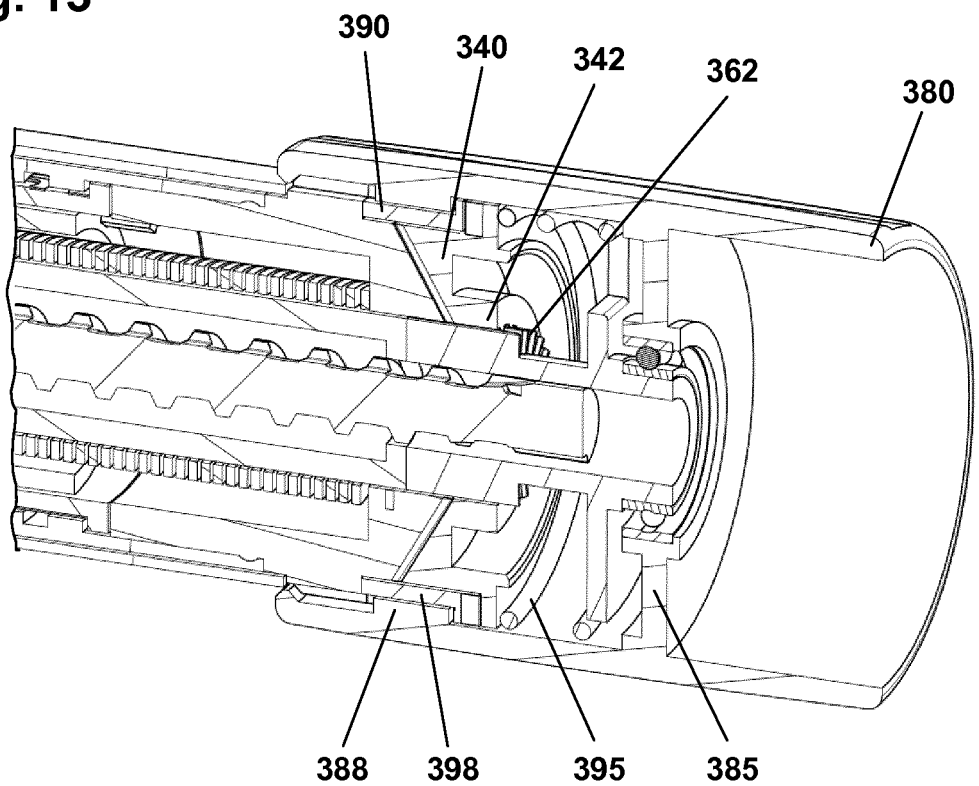
FIG. 13 shows in cross-section the second exemplary embodiment in an assembled state.

Turning to FIGS. 12 and 13 the proximal portion of a partly and fully assembled device is shown. FIG. 12 shows a tubular main housing 309 to which the housing base member 301 is attached, the drive-lift control member 390, the drive tube 360 and a thereon mounted ball bearing 365, a helical drive spring 355 arranged around a portion of the drive tube and being connected to the spring base housing member 301 respectively the drive tube, a threaded piston rod 320 arranged inside the drive tube 360 and a scale drum 370 in threaded engagement with the housing main. In FIG. 13 further the transmission member 340, the dose setting member 380 and the return spring 395 have been mounted. Corresponding to the first embodiment the distal portion of the device comprises a piston drive member and a drive coupling arrangement (not shown).

More specifically, the dose setting member 380 is mounted axially moveable relative to the housing member 301 between a proximal position (as shown in FIG. 13) in which the splines 388 engages the splines 398 on the drive-lift control member 390, this allowing the dose setting member to rotate during dose setting, and a distal position in which the splines 388 engages the splines 308 on the housing member, this rotationally locking the dose setting member to the housing member. In the shown embodiment the dose setting member remains in splined connection with control member. Further, the dose setting member is mounted axially locked but rotationally free on the drive tube proximal end by means of a ball bearing 365, this allowing the dose setting member to serve as a combined dose setting and actuation member as will be described below. The proximal open end of the dose setting member is closed by a circular plate (not shown).

The transmission member 340 is mounted non-rotationally on the drive tube by means of a splined connection 342, 362 allowing the transmission member to move axially relative to both the drive tube and the dose setting member. A bias means in the form of a return spring 395 is arranged between the transmission member and the dose setting member partition wall 385, the return spring urging the transmission member ratchet teeth 343 into engagement with the housing member ratchet teeth 303 as shown. As appears, in the engaged position the ratchet prevents the transmission member, and thus the drive tube, from being turned counter-clockwise. As shown in FIG. 12 the drive-lift control member 390 is during dose setting rotationally locked to the dose setting member via the splined connection, and the drive-lift teeth of the drive-lift member and the transmission member are urged into engagement by the return spring.

When setting a dose the dose setting member in its proximal position is rotated clockwise. As the drive surfaces 397 of the drive-lift control member 390 are in engagement with the corresponding drive surfaces 347 on the transmission member 340 the latter is forced to rotate together with the dose setting member to the desired rotational position, this resulting in the transmission member ratchet teeth 343 passing over the housing member ratchet teeth 303 during which the transmission member is moved back and forth due to the inclined ratchet teeth, the return spring 395 and the splined connection with the drive tube. The dose can be set in increments corresponding to one ratchet tooth which e.g. for a given insulin delivery device typically will correspond to one unit (IU) of insulin formulation.

When decreasing a set dose the dose setting member is rotated counter-clockwise whereby a gap is created between the drive surfaces on the drive-lift control member 390 respectively the transmission member 340. However, as the inclined lift surfaces 396 of the drive-lift control member are in engagement with the corresponding lift surfaces 346 on the transmission member the latter is moved proximally against the return spring until the transmission member ratchet teeth just disengages the housing member ratchet teeth, at which point the force from the strained drive spring 355 will rotate the drive tube counter-clockwise and thereby also the transmission member, this resulting in the inclined lift surfaces disengaging each other. As a consequence the transmission member can be moved distally by the return spring whereby the ratchet teeth will re-engage, this corresponding to the previously set dose having been decreased by one increment. If the user continuous to rotate the dose setting member counter-clockwise the set dose will continue to be reduced by one increment for each back and forth movement of the transmission member. At the same time the scale drum is also rotated counter-clockwise and the dose size shown in the display window is reduced correspondingly.

To expel a set dose of drug the combined dose setting and actuation member 380 is moved distally against the force of the return spring 395 whereby at first the dose setting member connects to the splines 308 of the housing spring base member 301 to prevent further adjustment of the set dose, secondly the distal end of the drive tube 360 engages the piston driver via the drive coupling, and thirdly the drive tube splines disengages the transmission member splines 342, this allowing the strained spring 355 to rotate the drive tube and thereto coupled piston driver and piston rod 320 counter-clockwise, this resulting in the piston rod being moved distally through a threaded housing nut. When the user releases the pressure on the combined dose setting and actuation member the return spring serves to return the member and drive tube in the proximal direction and thereby firstly re-engage the splined connection between the drive tube and the transmission member and secondly dis-engage the drive tube from the piston driver, this movement also allowing a partly expelled dose to be paused.

With reference to FIGS. 14-21 a third exemplary embodiment of the present invention will be described. The mechanism basically comprises a housing member 401, a ratchet member 440, a drive tube 460, a torsion spring 455 arranged between the housing and the drive tube, a piston drive member 430, a combined dose setting and release member 480 (in the following also: dose setting member) and a bias means in the form of a return spring 495. Similar to the second embodiment the functionality of the ratchet mechanism and the drive-lift mechanism have been designed as two distinctive mechanisms, however, as will be apparent from the below detailed description of the third embodiment the different ratchet surfaces have been arranged on different members and in different locations compared with the second embodiments. Otherwise the general working principles of the three embodiments are the same as will be apparent from the detailed description of the working principle given below, however, first some of the central components of the dose setting mechanism will be described in detail.

Figure 14:
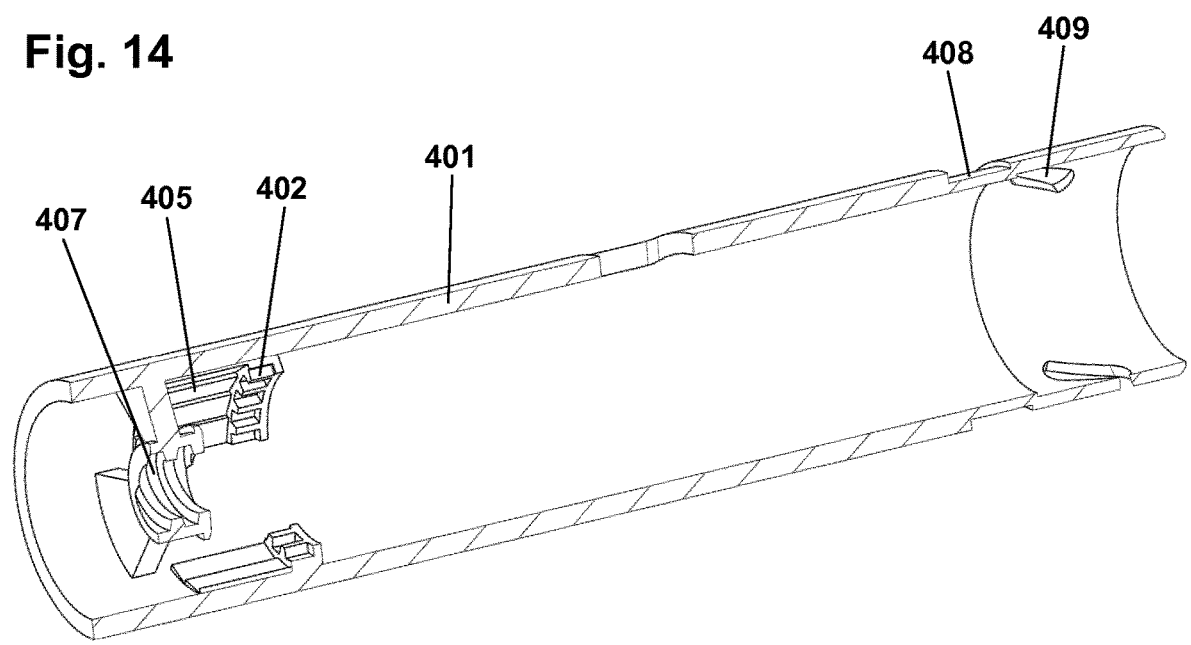
FIG. 14 shows a housing member of a third exemplary embodiment of a drug delivery device.

Turning to FIG. 14 a tubular housing member 401 defining a longitudinal reference axis is shown. The housing member comprises at the distal end portion a stationary threaded housing nut portion 407 connected to the housing wall by three supports (two shown) as well as a three spline segments 402 (two shown) circumferentially arranged corresponding to the openings between the nut supports. Each spline segment comprises a number of splines which are open in the distal direction and closed in the proximal direction by spline stop surfaces. Corresponding to each spline segment a circumferential ratchet segment 405 is formed on the inner surface of the housing wall distally of the ratchet segments. As will be described below the ratchet segments are arranged to engage the piston drive member and are thus not part of the dose setting ratchet mechanisms. The housing further comprises a circumferential groove 408 adapted to engage the dose setting member and arranged between the groove and the proximal housing end a number of inclined slots 409 (two shown) adapted to engage a spring housing (see below).

Figure 15:
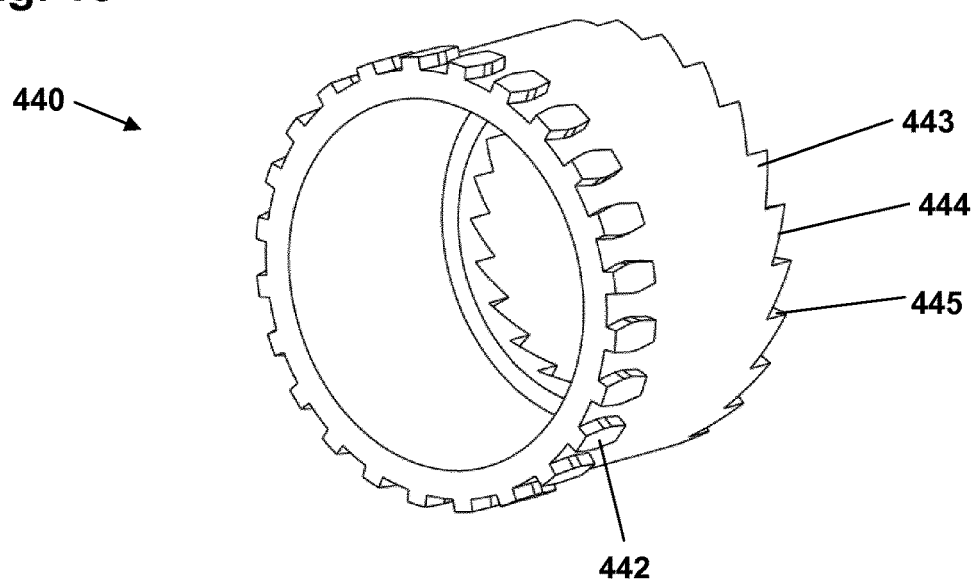
FIG. 15 shows a ratchet part of the third exemplary embodiment of a drug delivery device.

Turning to FIG. 15 a tubular ratchet member 440 is shown. The ratchet member comprises a circumferential proximal edge with a plurality of ratchet teeth structures 443 (here: 24), each tooth having a triangular configuration with an inclined ratchet surface 444 and a stop surface 445 oriented perpendicularly to the housing member cross-sectional plane. The ratchet member further comprises a circumferential array of splines 442 adapted to engage the housing spline segments 402. In this way a first ratchet part coupled non-rotationally to the housing (when the splines are in engagement) and comprising a plurality of ratchet teeth is formed. As appears, in this embodiment the first ratchet part is not formed integrally with a housing member.

Figure 16:
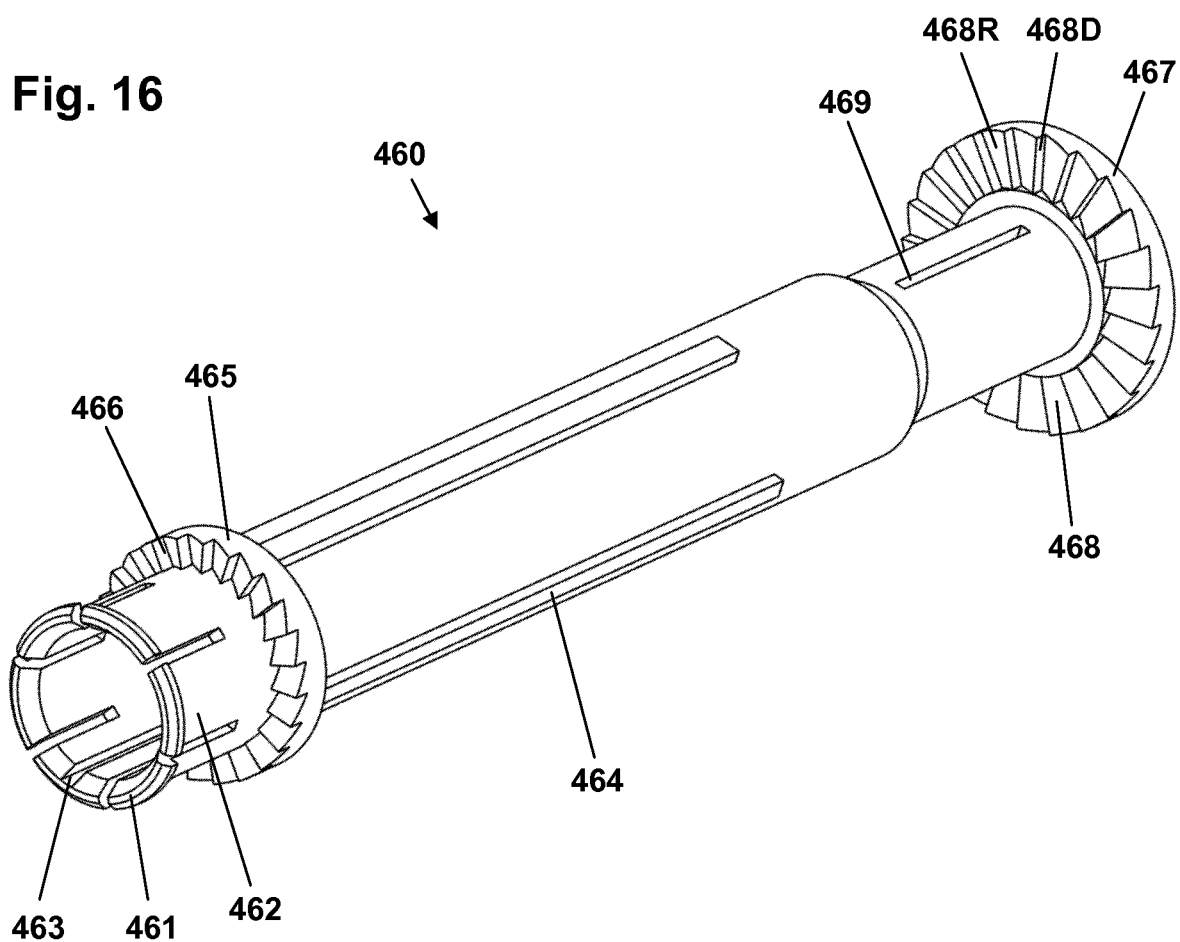
FIG. 16 shows a drive member of the third exemplary embodiment.

FIG. 16 shows the drive tube 460 having a distal-most circumferential flange 461, a distal circumferential flange 465 and a proximal circumferential flange 467. The distal flange comprises a distally-facing surface on which a first plurality of ratchet teeth structures 466 (here: 24) is arranged, each tooth having a triangular configuration with an inclined ratchet surface and a stop surface oriented perpendicularly to the housing member cross-sectional plane, the ratchet teeth being configured to interface with the corresponding ratchet teeth 443 on the ratchet member 440 to thereby provide a one-way dose setting ratchet assembly. In this way a second ratchet part is formed integrally with the drive tube. The proximal flange 467 also comprises a distally-facing surface on which a second plurality of ratchet teeth structures 468 (here: 24) is arranged, each tooth 468 having a triangular configuration with an inclined ratchet lift (release) surface 468R and a ratchet drive surface 468D oriented perpendicularly to the housing member cross-sectional plane, the ratchet teeth being configured to interface with corresponding ratchet teeth 488 on the dose setting member 480 (see below) to thereby provide a drive-lift ratchet assembly. The drive tube further comprises a slot 469 for attaching the inner end of the drive spring. The proximal end of the drive tube is closed by an end wall having a central conical dimple 467' (see FIG. 21). The distal-most portion of the drive tube is provided with a number of longitudinal slots forming a number of flexible fingers 462, this allowing the thereon formed flange segments to flex outwardly (see below). The drive tube further comprises a number of outer drive splines 464 adapted to interface with a scale drum and a pair of inner drive splines 463 adapted to interface with an end-of-content element.

Figure 17:
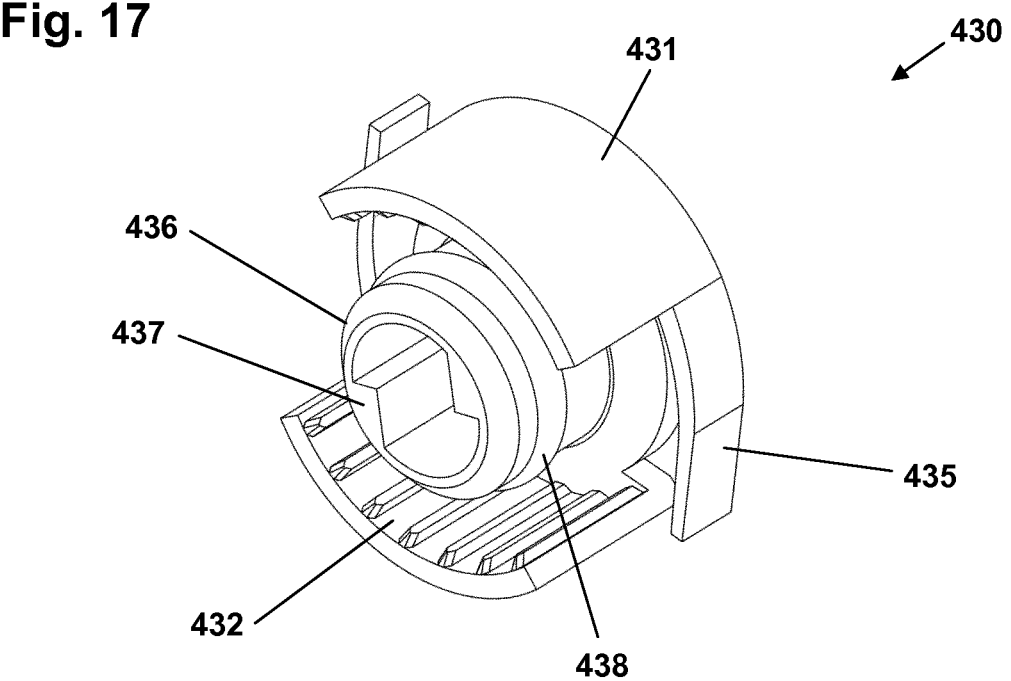
FIG. 17 shows a further ratchet part of the third exemplary.

FIG. 17 shows the piston drive member 430 comprising an inner drive portion 436 and two circumferential outer spline segments 431 each having a flexible ratchet arm 435 for interfacing with the housing ratchet segments 405. The inner drive portion comprises a pair of opposed drive structures 437 adapted to non-rotationally engage the piston rod as well as a circumferential rounded ridge 438 adapted to engage the flange fingers 462 (see below). Each spline segment comprises a plurality of longitudinal splines adapted to axially cooperate with the ratchet member splines 442 (see below).

Figure 18:
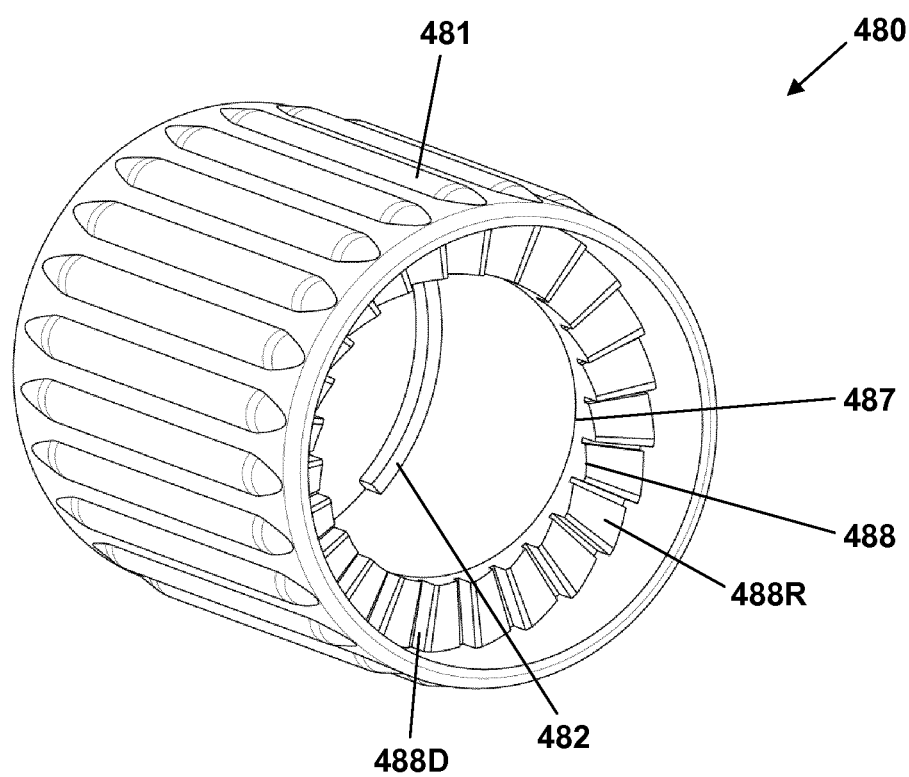
FIG. 18 shows a dose setting member of the third exemplary embodiment.

FIG. 18 shows the dose setting member 480 having a generally tubular configuration with an outer cylindrical surface with a plurality of longitudinally arranged ridges 481 providing a gripping surface, and an inner cylindrical surface comprising at the distal end a number of flange segments 482 adapted to cooperate with the housing circumferential groove 408 to control axial movement, and at the proximal end a circumferential flange 487 comprising a proximally-facing surface on which a plurality of ratchet teeth structures 488 (here: 24) is arranged, each tooth having a triangular configuration with an inclined ratchet lift (release) surface 488R and a ratchet drive surface 488D oriented perpendicularly to the housing member cross-sectional plane, the ratchet teeth being configured to interface with corresponding ratchet teeth 468 on the drive tube proximal flange 467 to thereby provide a drive-lift ratchet assembly.

Figure 19:
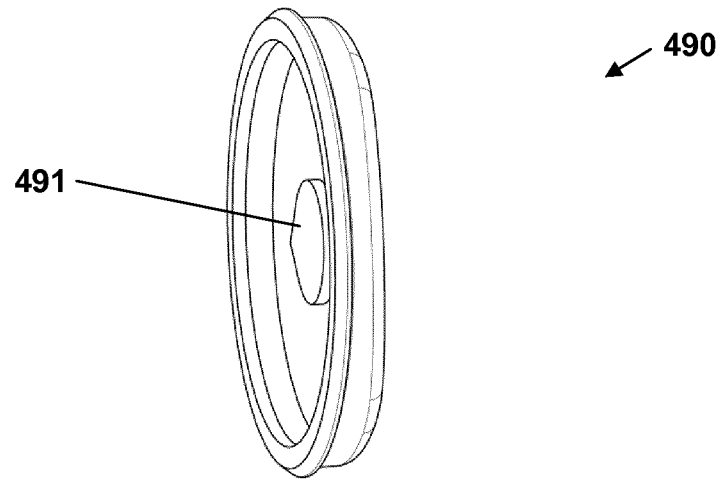
FIG. 19 shows a release button member of the third exemplary embodiment.

FIG. 19 shows a release button member 490 adapted to be axially fixed in the proximal opening of the dose setting member, the distal surface thereof comprising a pointed structure 491 adapted to engage a corresponding receiving cavity on the proximal end of the drive tube during actuation.

Figure 20:
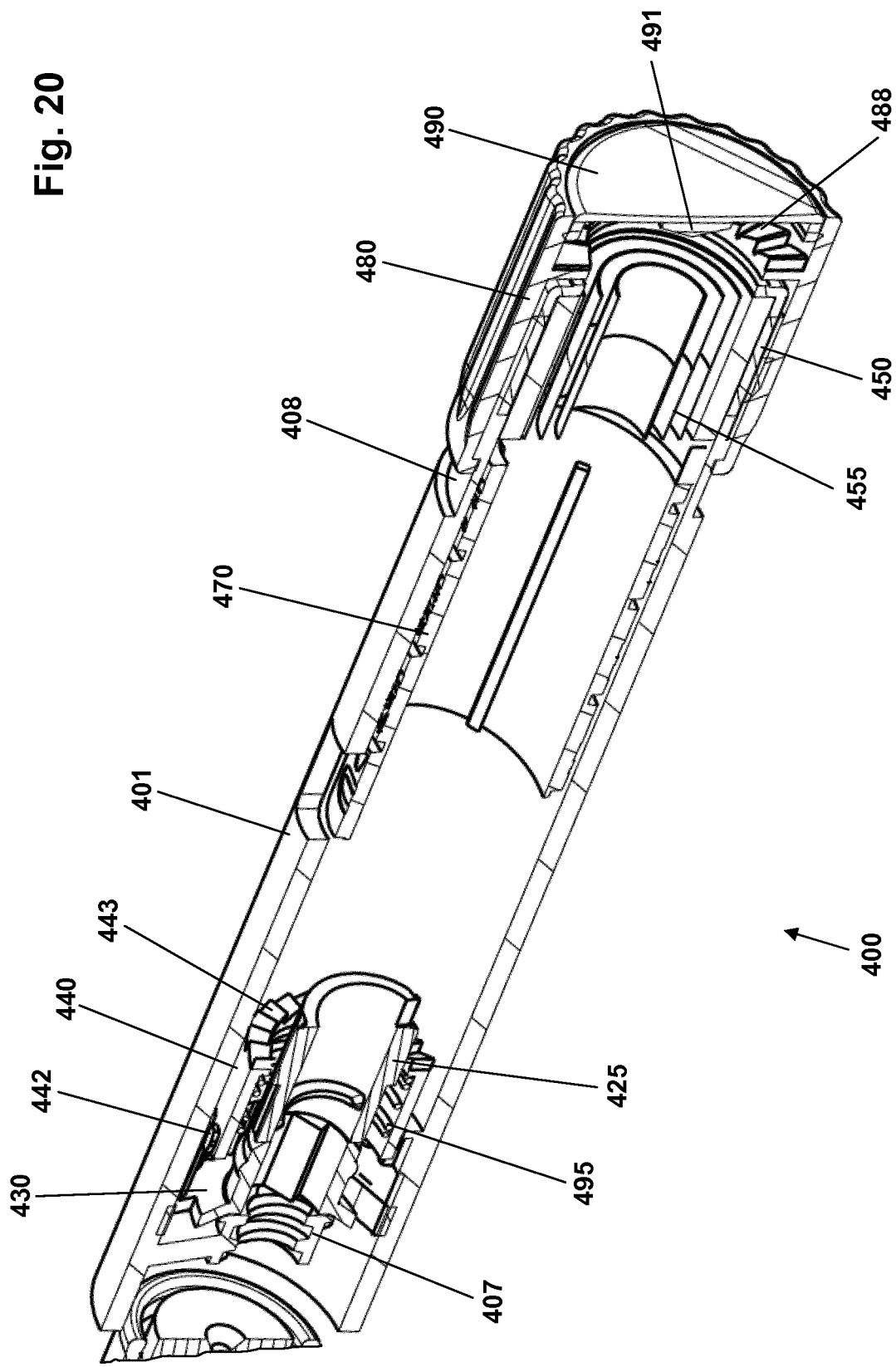
FIG. 20 shows in cross-section the third exemplary embodiment in a partly assembled state.

Turning to FIGS. 20 and 21 the main portion of a partly and fully assembled device is shown in an initial state. FIG. 20 shows the tubular housing 401, the ratchet member 440, a return spring 495, the piston drive member 430, an end-of-content member 425, a clock-type torsion drive spring 455 mounted in a cup-shaped spring housing 450 and connected to the spring housing respectively the drive tube (when mounted), the dose setting member 480 with the release button member mounted, as well as and a scale drum 470 in threaded engagement with the housing main. The dose setting member is coupled to the housing via the flange segments 482 arranged in the circumferential groove 408. As described above for the first embodiment, the spring housing 450 is coupled to the main housing via inclined slots 409 whereby the spring housing is moved proximally by the spring torque and into engagement with the dose setting member flange 487 thereby providing a proximally-directed biasing force on the dose setting member ensuring that it is moved to its proximal-most position in the housing groove 408. The piston drive member 430 is mounted in abutment with the housing nut portion 407. The ratchet member splines 442 are arranged in the housing splines 402 in abutment with the spline stop surfaces as well as in engagement with the piston drive member splines 432, the three components thereby being rotationally locked to each other in the shown state. In FIG. 20 the proximally-facing ratchet member teeth structures 443 as well as the proximally-facing dose setting member teeth structures 488 can be seen.

In FIG. 21 the drive tube 460 and the threaded piston rod 420 arranged inside the drive tube have been mounted, the distally facing ratchet surfaces 466, 468 of the drive tube thereby engaging the corresponding ratchet surfaces on the ratchet member respectively the dose setting member. At the distal end a piston rod foot 421 is mounted to the piston rod. The return spring 495 is arranged in the circumferential space between the ratchet member and the drive tube distal portion and exerts a proximally directed force on the ratchet member respectively a distally directed force on the drive tube via the distal flange 461. Corresponding to the above description of the individual members, the piston rod is in threaded engagement with the drive nut 407 and the end-of-content member 425 as well as non-rotationally engaged with the inner drive portion 436 of the piston drive member 430. The drive tube is in non-rotational engagement with the scale drum 470 and the end-of-content member 425, as well as being connected to the inner end of the drive spring 455.

When setting a dose the dose setting member 480 in its proximal position is rotated clockwise. As the drive surfaces of the drive-lift ratchet teeth 488 are in engagement with the corresponding drive surfaces on drive tube drive-lift ratchet teeth 468 the drive tube is forced to rotate together with the dose setting member to the desired rotational position, this resulting in the drive tube ratchet teeth 466 passing over the ratchet member teeth 443 during which the ratchet member is moved back and forth due to the inclined ratchet teeth, the return spring 495 and the splined connection 442, 402 with the housing. The dose can be set in increments corresponding to one ratchet tooth which e.g. for a given insulin delivery device typically will correspond to one unit (IU) of insulin formulation. At the same time the scale drum is rotated helically to display the set dose.

When decreasing a set dose the dose setting member 480 is rotated counter-clockwise which in analogy with the above-described embodiments would result in the ratchet flange 467 being lifted proximally against the force of the return spring 495, but due the specific design of the third embodiment the lift movement may also take place between the ratchet surfaces of the dose setting ratchet assembly 466, 443 whereby the ratchet member would be lifted, i.e. moved distally against the force of the return spring. Also a combination of the two movements may take place. However, in the described embodiment the interacting structures and surfaces have been designed such that only the drive tube is lifted proximally against the force of the return spring. Corresponding to the above-described embodiments, when the ratchet teeth just disengages the force from the strained drive spring 455 will rotate the drive tube counter-clockwise, this resulting in the inclined lift surfaces disengaging each other. As a consequence the drive tube can be moved distally by the return spring whereby the ratchet teeth will re-engage, this corresponding to the previously set dose having been decreased by one increment. If the user continuous to rotate the dose setting member counter-clockwise the set dose will continue to be reduced by one increment for each back and forth movement of the drive tube. At the same time the scale drum is also rotated counter-clockwise and the dose size shown in the display window is reduced correspondingly.

To expel a set dose of drug the combined dose setting and actuation member 480, 490 is moved distally against the proximally-directed return force from the spring housing 450 as this is being rotated in the inclined housing slots 409, whereby at first the drive-lift ratchet teeth disengage, and secondly the pointed structure 491 engages the receiving cavity on the proximal end of the drive tube whereby further distal movement of the combined dose setting and actuation member results in the drive tube being moved distally against the proximally-directed force from the spring housing. As the drive tube is moved distally the distal flexible fingers 462 engages the circumferential rounded ridge 438 of the piston drive member and are thereby expanded laterally to provide a distal stop for the ratchet member (see below). Together with the drive tube also the ratchet member 440 is moved distally, initially in splined engagement with both the housing splines 402 and the piston drive member splines 432. Subsequently the ratchet member splines 442 disengages the housing splines 402, this allowing the strained spring 455 to rotate the drive tube and thereto coupled piston drive member 430 and piston rod 420 counter-clockwise, this resulting in the piston rod being moved distally through the threaded housing nut 407.

When the user releases the pressure on the combined dose setting and actuation member the return force from the spring housing 450 will serve to return the drive tube in the proximal direction. Due to the expanded flexible fingers on the drive tube it is ensured that the ratchet member 430 is also moved proximally to thereby re-engage the splined connection between the ratchet member and the housing, this movement also allowing a partly expelled dose to be paused. Finally the combined dose setting and actuation member disengages the drive tube and the drive-lift ratchet re-engages.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device comprising or adapted to receive a drug-filled cartridge, comprising:
   a housing,
   an expelling assembly comprising:
      a piston rod adapted to engage and axially displace a piston in a loaded cartridge in a distal direction to thereby expel a dose of drug from the cartridge,
      a drive member defining a reference axis,
      a drive spring coupled to the drive member,
      dose setting structure allowing a user to simultaneously set a dose amount to be expelled and strain the drive spring correspondingly by rotation of the drive member, and
      release structure adapted to release the strained drive spring to rotate the drive member to expel the set dose amount,
   wherein the dose setting structure comprises:
      a dose setting member adapted to rotate in a first direction to set a dose, and rotate in an opposed second direction to reduce a set dose, and
      a releasable one-way ratchet mechanism allowing the drive member to be rotated in the first direction, comprising:
         a first ratchet part comprising a plurality of ratchet teeth, the first ratchet part being non-rotationally coupled to the housing during dose setting,
         a second ratchet part comprising a plurality of ratchet teeth adapted to rotationally engage the ratchet teeth on the first ratchet part, the second ratchet part being non-rotationally coupled to the drive member during dose setting, the first and second ratchet parts being axially moveable relative to each other during dose setting, and
         a compression spring for axially biasing the first and second ratchet parts into engagement with each other,
   wherein the dose setting structure further comprises:
      control structure adapted to rotate the second ratchet part in the first direction to thereby set a dose when the dose setting member is rotated in the first direction, and move the first and second ratchet parts axially out of engagement with each other when the dose setting member is rotated in the second direction, the control structure comprising:
         a drive-release ratchet having a plurality of ratchet drive surfaces and a plurality of ratchet release surfaces inclined relative to a rotational reference plane, and
         a control ratchet comprising a plurality of control drive surfaces and a plurality of control release surfaces inclined relative to the rotational reference plane,
   wherein:
      the control drive surfaces are cooperating with the ratchet drive surfaces to rotate the second ratchet part in the first direction when the dose setting member is rotated in the first direction, and the control release surfaces are slidingly cooperating with the ratchet release surfaces to axially move the first and second ratchet parts axially out of engagement with each other against the bias of the compression spring when the dose setting member is rotated in the second direction, and whereby, when the first and second ratchet parts have been axially dis-engaged, the drive spring will rotate the second ratchet part in the second direction to thereby reduce the set dose, the compression spring moving the first and second ratchet parts axially into engagement with each other again, this resulting in the set dose being reduced corresponding to one tooth of the ratchet mechanism.

2. The drug delivery device as in claim 1, wherein:
the first ratchet part is integral with the housing, and
the second ratchet part is rotationally released from the drive member during dose expelling.

3. The drug delivery device as in claim 2, wherein:
the drive-release ratchet is integral with the second ratchet part, and
the control ratchet is integral with the dose setting member.

4. The drug delivery device as in claim 3, wherein the ratchet drive surfaces, the ratchet release surfaces and the second ratchet part teeth are arranged on the same circumference.

5. The drug delivery device as in claim 1, wherein:
the first ratchet part is integral with the housing,
the second ratchet part is rotationally released from the drive member during dose expelling,
the drive-release ratchet is integral with the second ratchet part, and
the control ratchet is coupled non-rotationally but axially moveable to the dose setting member.

6. The drug delivery device as in claim 5, wherein the dose setting member is a combined dose setting and release member being moveable from a proximal dose setting position to a distal spring release position.

7. The drug delivery device as in claim 1, wherein:
the first ratchet part is axially moveable relative to the housing, and
the second ratchet part is integral with the drive member.

8. The drug delivery device as in claim 7, wherein the first ratchet part is moveable from a proximal dose setting position in which it is non-rotationally coupled to the housing, to a distal spring release position in which it is allowed to rotate relative to the housing.

9. The drug delivery device as in claim 1, wherein:
the first ratchet part is axially moveable relative to the housing,
the second ratchet part is integral with the drive member,
the drive-release ratchet is integral with the drive member, and
the control ratchet is integral with the dose setting member.

10. The drug delivery device as in claim 9, wherein the dose setting member is a combined dose setting and release member being moveable from a proximal dose setting position to a distal spring release position.

11. The drug delivery device as in claim 1, wherein the drive spring is a torsion spring.

* * * * *